(12) United States Patent
Haupt et al.

(10) Patent No.: US 6,413,230 B1
(45) Date of Patent: Jul. 2, 2002

(54) MEDICAL INSTRUMENT FOR TREATING BIOLOGICAL TISSUE

(75) Inventors: Gerald Haupt, Castrop; Andreas Menne, Meersburg; Manfred Schulz, Ueberlingen, all of (DE)

(73) Assignee: Ferton Holding (CH)

( * ) Notice: Subject to any disclaimer, the term of this patent is extended or adjusted under 35 U.S.C. 154(b) by 0 days.

(21) Appl. No.: 09/446,097

(22) PCT Filed: Jun. 3, 1998

(86) PCT No.: PCT/EP98/03317

§ 371 (c)(1),
(2), (4) Date: Feb. 22, 2000

(87) PCT Pub. No.: WO98/57707

PCT Pub. Date: Dec. 23, 1998

(30) Foreign Application Priority Data

Jun. 17, 1997 (DE) .......................................... 197 25 477

(51) Int. Cl.[7] .................................................. A61N 7/00
(52) U.S. Cl. ............................................................ 601/2
(58) Field of Search ........................... 601/2–4; 606/128

(56) References Cited

U.S. PATENT DOCUMENTS 5,160,336 A  11/1992 Favre

FOREIGN PATENT DOCUMENTS

EP  0 317 507 A1  5/1989
WO  WO 96/33661  10/1996

OTHER PUBLICATIONS (E–E1) Biomedizinische Technik—Band 25 9/80, 3 pages with partial translation.

(E–E2) Externe herzstimulation durch Druckpulse 1/81 3 pages w/partial translation.

(E–E3) Bundesministerium fur Forschung und Technologies Dec. 1983, 14 pages w/partial translation.

(E–E5) Swiss Lithoclast (EMS–Electro Medical System) 12 pages.

*Primary Examiner*—Ruth S. Smith
(74) *Attorney, Agent, or Firm*—Diller, Ramik & Wight

(57) ABSTRACT

The invention relates to a medical instrument for treating biological tissue, comprising a device for generating extracorporeal pressure waves and a transmission element (2) for injecting pressure waves into the bodies of living organisms. According to the invention the transmission element (2) has a blunt probe tip (22) with a flat exit surface (24) which injects non-focused mechanically generated pressure waves into the biological tissue.

31 Claims, 1 Drawing Sheet

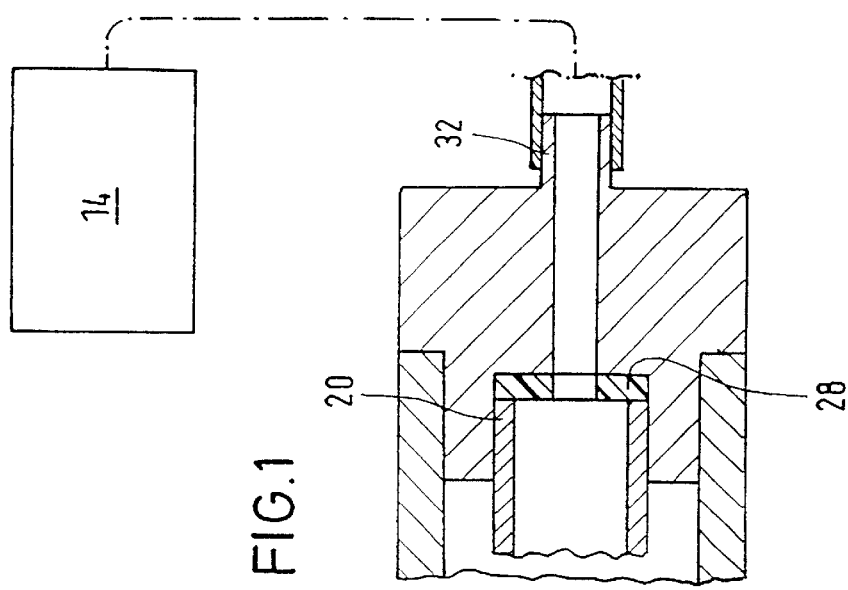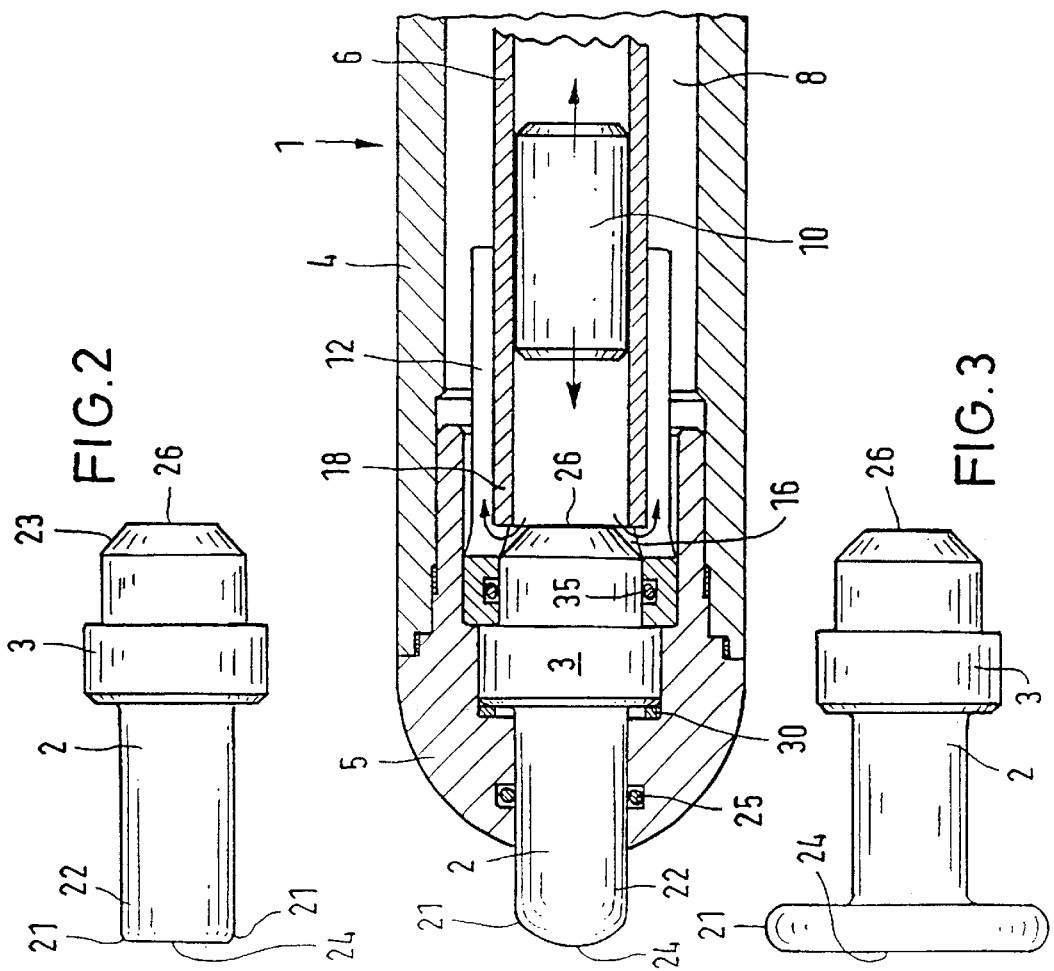
FIG.1
FIG.2
FIG.3

MEDICAL INSTRUMENT FOR TREATING BIOLOGICAL TISSUE

BACKGROUND OF THE INVENTION

Such instruments serve for accelerating the healing process in the case of bone fractures, enthesopathies, tendopathies but also periodontosis by means of pressure or shock waves. Another application is the pain therapy in the near-bone soft tissue area of the attitude and locomotor system.

In the extracorporeal pressure wave generators known so far a pressure or shock wave is generated in the focus of an acoustical reflector, e.g. by means of spark discharge, with the wave being focused via the reflector onto the object to be treated with the waves. It is assumed that the pressure waves produce microlesions in the biological tissue, which induce the body to take regeneration measures.

Known pressure pulse sources use focused shock waves and are capable of producing an effect only in the narrow focal area. A satisfactory result of treatment requires however uniform treatment with waves of the entire bone fracture area. This necessitates a complex motion mechanism for the pressure pulse source and is very time-consuming due to the repeated search for the treatment positions.

In the pain therapy another problem with the use of known pressure pulse sources is encountered. The localisation systems applied during the treatment to localise the area to be treated (ultrasonic and X-ray systems) are not capable of exactly indicating the source of pain and the doctor thus injects a large number of individual pulses into the assumed source of pain.

SUMMARY OF THE INVENTION

It is therefore the object of the present invention to configure a pressure wave generator allowing uniform distribution of the pressure wave energy to a large spectrum in a simple and inexpensive way.

The invention provides in an advantageous manner for the transmission element comprising a blunt probe tip with a flat exit surface which injects a mechanically generated pressure wave into the biological tissue. The pressure or shock wave can propagate from there to its application location without the transmission element being in direct contact with the application location. The invention aims at not focusing the pressure waves thus allowing the waves to be injected into a large area. The medical instrument is particularly suitable for treatments during which the probe tip can be arranged on the body surface very closely to the application location, such as a tennis elbow, a heel spur or periodontosis.

It is preferably provided for the pressure wave generator to comprise a reciprocating beater part guided in a housing by means of an actuating element with the beater part exerting one or several impulses onto the transmission element thus inducing a pressure wave into the transmission element due to the impulse, which propagates to the exit boundary surface of the blunt probe tip of the transmission element. Accordingly the pressure wave is mechanically generated in a simple way. Owing to the rapid motion of the probe tip a pressure wave with high pressure peak values can be generated. The pressure wave propagates in the biological tissue and is not focused. The pressure waves generated in such a system do not reach the short rise times of those generated by pressure wave generators with focused pressure wave but they are not considerably weaker in their maximum pressure peak. The non-focused pressure wave radially propagates up to the application location in the biological tissue.

Essential advantages of the invention are that the medical instrument is of simple and inexpensive design and the costs involved lie far below those for the previously known pressure wave generators.

The medical instrument can be executed as a small portable device which is easy to apply and can be placed onto the part of the body to be treated without any impediment. The device requires no consumables and in particular no locating means since the area to be treated lies near the probe tip.

The beater part is preferably arranged coaxially to the transmission element. This leads to direct pulse exchange between the beater part and the transmission element when the beater part strikes the entry boundary surface of the transmission element.

In particular in orthopedic applications it is of advantage to inject a plurality of individual pressure waves into the biological tissue to achieve an optimum effect. For this reason the actuating element is preferably executed in such a way that periodical reciprocating motion of the beater part is possible. The beating frequency amounts to approximately 1 to 30 Hz, preferably to approximately 6 to 20 Hz.

In a preferred embodiment the transmission element is axially and linearly guided in the housing with a spring/damping element being arranged between the transmission element and the housing. In this way decoupling of the transmission element from the housing in axial direction is realised. Furthermore this spring/damping element restores the transmission element to its home position after each pressure wave injection and delimits its excursion. Injection of the pressure wave into the biological tissue does not require a large stroke of the exit boundary surface of the transmission element but should rather be effected only as a result of an elongation of the transmission element and not as a result of its displacement. Thus the injection of the pressure wave into the biological tissue occurs without considerable movement of the probe tip.

The impulses acting on the entry boundary surface of the transmission element induce the probe tip to be displaced by less than 1 mm, preferably less than 0.5 mm due to compression of a damping element interposed between the transmission element and the housing.

Between the beater part and the transmission element an intermediate element may be arranged which transmits the impulse from the beater part to the transmission element. This intermediate element may serve for offering better screening of the actuating element towards the application area or for changing the direction of the pressure wave or for influencing the pressure wave characteristic.

At the proximal end of the beater part guide a magnetic holder for the beater part may be arranged, which retains the beater part in the proximal end position until it is accelerated again by the actuating means.

The blunt probe tip preferably comprises a flat exit boundary surface with rounded edges. The exit boundary surface of the transmission element is executed as large as possible to achieve high efficiency during transmission of the pressure wave. The edges are rounded to prevent lesions of the skin surface.

The probe tip may also have a concave exit boundary surface with rounded edges.

In another embodiment of the transmission element the exit boundary surface may have a considerably larger diameter than the entry boundary surface. Such an exit boundary surface ensures a large transmission surface for injection of the pressure wave so that the injected specific pressure wave energy is reduced to take care of the skin surface.

Between the probe tip and the injection location on the biological tissue an impedance matching medium may be arranged which improves injection of the pressure wave into the biological tissue. A suitable pasty impedance matching medium is, for example, an ultrasonic gel or other pasty substance, such as vaseline.

For impedance matching purposes the transmission element may be made up of various materials which improve the transmission behaviour. The selection of suitable materials may influence the transmission behaviour of the pressure wave, and the transmission element respectively and thus the injection into the biological tissue. Manufacturing the single-piece transmission element from various materials aims at low-loss injection of the pressure wave into the body thus allowing impedance matching.

The length of the transmission element may range between approximately 20 and 100 mm. Different exchangeable transmission elements allow adjustment to the desired method of treatment.

In the following embodiments of the invention are explained in detail with reference to the drawings in which;

BRIEF DESCRIPTION OF THE DRAWINGS

FIG. 1 shows a cross-sectional representation of the medical instrument and

FIGS. 2 and 3 show alternative embodiments of the transmission element.

DESCRIPTION OF THE PREFERRED EMBODIMENTS

The handpiece 1 shown in FIG. 1 comprises a housing 4 accommodating a pneumatic cylinder 6 in which a beater part 10 is reciprocated between two end positions with the aid of pneumatic actuating means 14 in connection with a dynamic pressure chamber 8 encircling the cylinder 6 in a coaxially ring-shaped manner. Alternatively the beater part 10 can be accelerated hydraulically, mechanically, electromagnetically or by other actuating means. In the case of electromagnetic acceleration of the beater part 10 it is possible to shorten the acceleration path which is approximately 100 to 200 mm long when a pneumatic actuator is employed.

In the proximal end position of the beater part 10 a magnetic holder 28 is arranged at the proximal end 20 of the cylinder 6, which can retain the metal beater part 10 in its proximal end position until a pneumatic pressure applied again via connection 32 accelerates the beater part 10 in the direction of the distal end 18 of the cylinder 6. The air upstream of the beater part as seen in the direction of motion of the beater part 10 is fed via an annular slot 16 located at the distal end 18 of the cylinder 6 to the dynamic pressure chamber 8. Owing to the acceleration of the beater part 10 the beater part strikes at a high end velocity of for example, 5 to 20 m/sec. the entry boundary surface 26 of a transmission element 2 arranged distally from the cylinder 6. The transmission element 2 comprises a metal probe with blunt probe tip 22 and a plane or concave exit boundary surface 24. The beater part 10 exerts one or several impulses onto the transmission element 2 which transmits the pressure wave induced by the beater part 10 to the exit boundary surface 24 and injects it there into the biological tissue.

The transmission element 2 is guided in the housing 4 linearly and preferably coaxially to the beater part 10. The housing 4 comprises an upper part 5 which can be unbolted for the purpose of exchanging the transmission element 2. The transmission element 2 is supported in a bore of the upper part 5 and sealed by means of an O-ring 25 in the front section of the upper part 5. An annular collar 3 of the transmission element 2 serves as abutment element with a spring/damping element 30 being arranged between the annular collar 3 of the transmission element 2 and the upper part 5 of the housing 4, which decouples in axial direction the transmission element 2 from the housing 4. Furthermore the spring/damping element 30 has a reset function for the transmission element 2 and presses it back into its proximate home position after each pressure wave application. At the same time it delimits its excursion during pressure wave application. For injection of the pressure wave into the biological tissue excursion of the transmission element is not required but even undesired in order to prevent lesions. The pressure, wave is to be injected into the biological tissue exclusively by the elongation of the transmission element 2 caused by pressure wave propagation.

The dynamic pressure building up in the dynamic pressure chamber 8 suffices—when the pressure prevailing at the pneumatic connection 32 is omitted—to return the beater part 10 from the distal end position at the transmission element 2 into the proximal end position at the magnetic holder 28. The pneumatic pressure at the connection 32 may amount to up to 0.5 Mpa (5 bar ). For the purpose of adjustment to certain lengths of the transmission element 2 or generation of a certain characteristic of the pressure wave different beater parts 10 with regard to length and mass and different maximum striking velocities of the beater part 10 may be selected.

The proximal entry boundary surface 26 of the transmission element 2 has substantially the same diameter as the beater part 10 whereas the exit boundary surface 24 may, for example, have a diameter which is larger than that of the entry boundary surface 26 by the factor 2. The length of the beater part 10 preferably exceeds its diameter. This results in better guiding qualities in the cylinder 6. Furthermore the mass can be simply varied with the aid of a different length of the beater part 10 without the diameter of the cylinder 6 and the entry boundary surface 26 of the transmission element 2 having to be changed.

The proximal end of the transmission element 2 is guided in a slotted sleeve 12 and radially sealed in this sleeve with the aid of an O-ring 35. The sleeve 12 forms, together with the proximal conical end of the transmission element 2, a connection between the dynamic pressure chamber 8 and the hollow space of the cylinder 6 located distally from the beater part 10.

The pressure waves are generated at a beating frequency of approximately 1 to 30 Hz, preferably 6 to 20 Hz. The probe tip 22 travels approximately 1 mm at maximum and preferably less than 0.5 mm.

FIG. 2 shows a transmission element 2 with a flat and blunt probe tip 22 with rounded edges.

In the embodiment of the transmission element 2 according to FIG. 3 the exit boundary surface 24 is considerably enlarged as compared with the entry boundary surface 26. The exit boundary surface 24 to entry boundary surface 26 diameter ratio amounts to approximately 2 to 3.

The medical instrument allows a therapeutical process to treat biological hard and soft tissue, in particular to heal osteopathy, such as bone fractures, enthesopathies, tendopathies and periodontosis, as well as pain therapy in the near-bone soft tissue area of the attitude and locomotor system to be carried out by non-focused injection of mechanically generated pressure waves via a blunt probe with flat exit boundary surface into the biological tissue.

The transmission element 2 may be made up of different materials in order to ensure low-loss injection of the pressure waves into the biological tissue and thus achieve impedance matching. It may be envisaged that the different materials are arranged in tandem as seen in axial direction.

Although a preferred embodiment of the invention has been specifically illustrated and described herein, it is to be understood that minor variations may be made in the apparatus without departing from the spirit and scope of the invention, as defined the appended claims.

What is claimed is:

1. A medical instrument for treating biological tissue comprising a device for generating extracorporeal pressure waves, said pressure waves generating device including a beater part (10) constructed and arranged for striking against a transmission element (2) for injecting the generated pressure waves into the bodies of living organisms, said transmission element (2) having a probe tip (22), said probe tip (22) including an exit boundary surface (24), said exit boundary surface (24) being one of a flat and convex surface configuration which induces non-focused mechanically generated pressure waves into biological tissue of living organisms, and said beater part (10) being accelerated to a velocity of more than 5 m/sec. when striking against said transmission element (2) and displacing said probe tip (22) by less than 1 mm.

2. The medical instrument as defined in claim 1 including actuating means (14) for accelerating said beater part (10) in a direction for striking against said transmission element (2).

3. The medical instrument as defined in claim 2 wherein said beater part (10) travels in a first direction for striking against said transmission element (2) and moving said transmission element (2) in said first direction, and means (30) for moving said transmission element (2) in a second direction opposite said first direction to thereby effect reciprocal movement of said transmission element (2).

4. The medical instrument as defined in claim 3 including means (28) for holding said beater part (10) at a position remote from said transmission element (2).

5. The medical instrument as defined in claim 3 including means (6) for guiding the movement of said beater part (10) toward and away from said transmission element (2).

6. The medical instrument as defined in claim 3 including means (6) for guiding the movement of said beater part (10) toward and away from said transmission element (2), and means (32) for introducing pressurized fluid into said guiding means (6) at an end thereof remote from said transmission element (2).

7. The medical instrument as defined in claim 2 wherein said beater part (10) travels in a first direction for striking against said transmission element (2) and moving said transmission element (2) in said first direction, means (30) for moving said transmission element (2) in a second direction opposite said first direction to thereby effect reciprocal movement of said transmission element (2), and said transmission element moving means (30) being defined by a biasing means.

8. The medical instrument as defined in claim 7 including means (28) for holding said beater part (10) at a position remote from said transmission element (2).

9. The medical instrument as defined in claim 7 including means (6) for guiding the movement of said beater part (10) toward and away from said transmission element (2).

10. The medical instrument as defined in claim 7 including means (6) for guiding the movement of said beater part (10) toward and away from said transmission element (2), and means (32) for introducing pressurized fluid into said guiding means (6) at an end thereof remote from said transmission element (2).

11. The medical instrument as defined in claim 2 including means (28) for holding said beater part (10) at a position remote from said transmission element (2).

12. The medical instrument as defined in claim 2 including means (6) for guiding the movement of said beater part (10) toward and away from said transmission element (2).

13. The medical instrument as defined in claim 2 including means (6) for guiding the movement of said beater part (10) toward and away from said transmission element (2), and means (32) for introducing pressurized fluid into said guiding means (6) at an end thereof remote from said transmission element (2).

14. The medical instrument as defined in claim 1 including actuating means (14) for accelerating said beater part (10) in a direction for striking against said transmission element (2), and means (6) for guiding the movement of said beater part (10).

15. The medical instrument as defined in claim 1 wherein the beater part (10) and the transmission element (2) are arranged in coaxial relationship to each other.

16. The medical instrument as defined in claim 1 wherein the beat frequency of the beater part (10) is substantially 1 to 30 Hz.

17. The medical instrument as defined in claim 1 wherein the beat frequency of the beater part (10) is substantially 6 to 20 Hz.

18. The medical instrument as defined in claim 1 wherein said beater part (10) travels in a first direction for striking against said transmission element (2) and moving said transmission element (2) in said first direction, and means (30) for moving said transmission element (2) in a second direction opposite said first direction to thereby effect reciprocal movement of said transmission element (2).

19. The medical instrument as defined in claim 1 wherein said beater part (10) travels in a first direction for striking against said transmission element (2) and moving said transmission element (2) in said first direction, means (30) for moving said transmission element (2) in a second direction opposite said first direction to thereby effect reciprocal movement of said transmission element (2), and said transmission element moving means (30) being defined by a biasing means.

20. The medical instrument as defined in claim 1 including means (28) for holding said beater part (10) at a position remote from said transmission element (2).

21. The medical instrument as defined in claim 1 including means (28) for magnetically holding said beater part (10) at a position remote from said transmission element (2).

22. The medical instrument as defined in claim 1 wherein said probe tip exit boundary surface (24) is substantially flat with a rounded peripheral edge (21).

23. The medical instrument as defined in claim 1 wherein said probe tip exit boundary surface (24) is substantially convex configuration with a rounded peripheral edge (21).

24. The medical instrument as defined in claim 1 wherein said probe tip exit boundary surface (24) is of a larger diameter than an entry boundary surface (26) of said transmission element (2).

25. The medical instrument as defined in claim 1 including an impedance matching medium disposed on said probe tip exit boundary surface (24).

26. The medical instrument as defined in claim 1 wherein said transmission element (2) is substantially 20–100 mm in length.

27. The medical instrument as defined in claim 1 wherein said transmission element (2) is constructed of different materials to effect selective impedance matching.

28. The medical instrument as defined in claim 1 wherein said transmission element (2) is constructed of different materials to effect selective impedance matching, and said different materials are disposed adjacent each other along the length of said transmission element (2).

29. The medical instrument as defined in claim 1 including means (6) for guiding the movement of said beater part (10) toward and away from said transmission element (2).

30. The medical instrument as defined in claim 1 including means (6) for guiding the movement of said beater part (10) toward and away from said transmission element (2), and means (32) for introducing pressurized fluid into said guiding means (6) at an end thereof remote from said transmission element (2).

31. The medical instrument as defined in claim 1 including means (6) for guiding the movement of said beater part (10) toward and away from said transmission element (2), means (32) for introducing pressurized fluid into said means (6) at a first end thereof remote from said transmission element (2), and means (16) at a second end (18) of said guiding means (6) remote from said first end of said guiding means (6) for venting fluid from said guiding means (6) during movement of said beater part (10) toward said transmission element (2).

* * * * *

UNITED STATES PATENT AND TRADEMARK OFFICE
CERTIFICATE OF CORRECTION

PATENT NO.    : 6,413,230 B1
DATED         : July 2, 2002
INVENTOR(S)   : Gerald Haupt et al.

It is certified that error appears in the above-identified patent and that said Letters Patent is hereby corrected as shown below:

Column 2,
Line 64, replace "The probe tip may also have a concave exit boundary"
with -- The probe tip may also have a convex exit boundary --.

Column 3,
Line 63, replace "probe tip 22 and a plane or concave exit boundary surface"
with -- probe tip 22 and a plane or convex exit boundary surface --.

Column 5,
Line 24, replace "boundary surface (24) being one of a flat and convex surface"
wth -- boundary surface (24) being one of a flat or convex surface --.

Signed and Sealed this

Twenty-eighth Day of June, 2005

JON W. DUDAS
*Director of the United States Patent and Trademark Office*